United States Patent [19]

Huang

[11] 4,272,410
[45] Jun. 9, 1981

[54] CATALYST FOR PREPARATION OF OXYGENATES FROM CARBON MONOXIDE AND HYDROGEN

[75] Inventor: Yun-Yang Huang, Troy, Mich.

[73] Assignee: Ethyl Corporation, Richmond, Va.

[21] Appl. No.: 89,978

[22] Filed: Oct. 31, 1979

Related U.S. Application Data

[63] Continuation of Ser. No. 38,470, May 14, 1979, Pat. No. 4,210,597.

[51] Int. Cl.$^3$ .................. B01J 21/04; B01J 23/58; B01J 23/64
[52] U.S. Cl. ............................................. 252/465
[58] Field of Search ......................................... 252/465

[56] References Cited

U.S. PATENT DOCUMENTS

| | | | |
|---|---|---|---|
| 3,649,566 | 3/1972 | Hayes et al. | 252/465 X |
| 4,096,164 | 6/1978 | Ellgen et al. | 260/449 R |

*Primary Examiner*—W. J. Shine
*Attorney, Agent, or Firm*—Donald L. Johnson; Joseph D. Odenweller; Willard G. Montgomery

[57] ABSTRACT

Oxygenated compounds can be prepared by contacting a gaseous mixture of hydrogen and carbon monoxide with a solid catalyst containing rhodium, tungsten and an alkali metal.

4 Claims, No Drawings

CATALYST FOR PREPARATION OF OXYGENATES FROM CARBON MONOXIDE AND HYDROGEN

CROSS REFERENCE TO RELATED APPLICATION

This application is a Continuation of co-pending U.S. Application Ser. No. 38,470 filed May 14, 1979, now U.S. Pat. No. 4,210,597.

BACKGROUND OF THE INVENTION

This invention relates to the Fischer-Tropsch type of reactions which are known in the art. More particularly, this invention relates to the reaction of carbon monoxide and hydrogen in the presence of rhodium-tungsten-sodium catalyst to produce oxygenated compounds.

U.S. Pat. No. 4,014,913 discloses a process for producing two carbon oxygenated compounds from carbon monoxide and hydrogen using a rhodium-manganese catalyst. U.S. Pat. No. 3,833,634 discloses a process for making polyfunctional oxygenated compounds, such as ethylene glycol from carbon monoxide and hydrogen using a rhodium-carbonyl complex catalyst.

Bhasin, et al, in *Synthesis Gas Conversion over Supported Rhodium and Rhodium-Iron Catalysts*, 54, J. of Catalysis, 120 (1978), disclose the use of supported rhodium and rhodium-iron catalysts to prepare acetic acid, acetaldehyde and ethanol.

SUMMARY OF THE INVENTION

The catalyst of this invention is composed of rhodium, tungsten, and a small amount of sodium. Rhodium-tungsten catalysts are fairly active for producing methane, but have little or no activity for the more valuable oxygenated compounds. When a small amount of an alkali metal is added to the catalyst, however, methanation activity substantially decreases and oxygenation activity substantially increases.

In accordance with this invention, a process is provided wherein a gaseous mixture of carbon monoxide and hydrogen is contacted with a rhodium-tungsten-alkali metal catalyst at a combination of reaction conditions correlated to achieve optimal selectivity for oxygenated compounds.

The major oxygenated compounds formed by this process are methanol, ethanol, n-propanol, methyl acetate, ethyl acetate and acetic acid. The term "oxygenated compounds" is meant to include these compounds. Since two carbon oxygenates are more commercially significant, it should be noted that methyl and ethyl acetate are readily converted to two carbon oxygenates and can be grouped with them for analysis.

DESCRIPTION OF THE PREFERRED EMBODIMENTS

Suitable reaction parameters for the process of this invention are within the ranges given for conventional synthesis gas conversions, so that conventional technology and equipment may be used. It is preferred that the reaction parameters be correlated to achieve optimal selectivity for oxygenated compounds. Selectivity as used herein refers to the percentage of carbon atoms converted from carbon monoxide to the specified compound or compounds. Oxygenated compound selectivities of from 10% to 60% can be achieved by the process of this invention.

By varying other parameters, the process of this invention may be carried out in a broad range of temperatures to obtain optimal results. However, it has been found that a preferred temperature range for the process of this invention, when other variables are within the preferred ranges disclosed herein, is from about 250° C. to about 350° C. A more preferred temperature range is from about 250° to about 300° C.

The ratio of hydrogen to carbon monoxide can vary from about 0.1 to 4. It is preferred that the ratio be less than 1, but greater than 0.1. This provides a reactant stream which is rich in carbon monoxide, which favors the formation of oxygenated compounds.

Pressure, like temperature, depends on the other variables employed. A preferred pressure range, based on the other parameters given, is from 100 to 5,000 psig. A more preferred range is from 150 to 2,000 psig. A most preferred range is from 200 to 1,600 psig.

Space velocity may be varied for various reasons, such as carbon monoxide conversion. A preferred range for gas hourly space velocity is from 200 to 20,000 for optimal production of oxygenated compounds.

It is preferred that the catalyst contain from 0.5 to 15 weight percent rhodium, from 1 to 25 weight percent tungsten, and from 0.5 to 10 weight percent of the alkali metal. Amounts less than 0.5 weight percent do not significantly increase oxygenate selectivity. The precise amounts of rhodium and tungsten employed are less significant.

A preferred alkali metal for use in the catalysts of this invention is sodium. It can be incorporated into the catalyst by conventional methods, such as, for example, impregnation, precipitation or coprecipitation as illustrated by the examples given below.

EXAMPLE 1

8.5100 g. of ammonium metatungstate $(NH_4)_6H_2W_{12}O_{40}\cdot XH_2O$ was dissolved in 50 ml. of distilled water. The solution was added to 50 g. of $\gamma$-alumina, and the mixture was briefly stirred and left at room temperature for 12 hours. It was then dried at 150° C. for 7 hours and calcined at 580° C. for 14 hours. This support contained 11% tungsten.

0.7820 g. of rhodium trichloride was dissolved in 15 ml. of distilled water. The solution was added to 10.118 g. of the tungsten-modified support. The mixture was left at room temperature for several days. It was then dried in an oven at 100° C. for 17 hours; reduced with hydrogen in a tubular furnace from 150° to 300° C. for 4 hours; calcined at 610° C. for 12 hours; and reduced with hydrogen again at 300° C. for 15 hours. By calculation the catalyst contained 3.05 weight percent rhodium and 10.66 weight percent tungsten. (A portion of this solid was used to compare with the sodium impregnated catalyst). This composition is hereinafter referred to as, Catalyst A. A second catalyst having the same composition as Catalyst A was prepared according to the foregoing procedure with the exception that rhodium nitrate was substituted for rhodium trichloride. This catalyst is designated Catalyst B. About 5 ml. of distilled water was added to 0.1014 g. of a 50% sodium hydroxide solution. This solution was then added to 2.8788 g. of the $\gamma$-alumina supported rhodium-tungsten formed above. The solid was dried on a hot plate for 1.5 hours, and contained 1.0 weight percent sodium by calculation. This composition is referred to hereinafter as Catalyst C.

EXAMPLE 2

12.0577 g. of sodium tungstate ($Na_2WO_4.2H_2O$) was dissolved in 50 ml. of distilled water. The solution was then added to 50 g. of γ-alumina. The mixture was allowed to stand for 18 hours at 25° C., and dried for 16 hours at 100° C. The modified support contained 11.06 weight percent tungsten and 2.77 weight percent sodium.

0.8035 g. of rhodium trichloride was dissolved in 15 ml. of distilled water. The solution was added to 10.213 g. of the tungsten-sodium modified support. The mixture was allowed to stand at room temperature for 22 hours. It was dried at 100° C. for 6 hours and calcined at 600° C. for 63 hours. The catalyst was reduced with hydrogen from 25° C. to 300° C. for 3 hours and at 400° C. for 2 hours. By calculation, the catalyst, hereinafter referred to as Catalyst D, contained 3.20 weight percent rhodium, 10.71 weight percent tungsten, and 2.68 weight percent sodium.

The reactions may be carried out in any reactor system capable of attaining the desired parameters, such as a conventional tubular flow reactor, or a "Berty" reactor. The reactors used for the process of this invention were of conventional design, with the modifications as set out below.

At pressures below 250 psig, a conventional tubular flow reactor was used. The reactor was vertically mounted, 14 inches long, with a ⅜ inch O.D. and was made of stainless steel tubing. The catalyst bed was 2 inches long. The system was equipped with a water cooled condenser at 15° C. and a Dry-Ice-pentanol bath at −80° C., serving as cold traps for liquid products.

About 3 g. of the catalyst, having a volume of about 4.7 cc., were placed in the reactor at the start of each run. The catalyst was treated with hydrogen at temperatures of from 140° C. to 410° C. for up to 15 hours at the start of each run. The catalyst was then cooled with hydrogen to the desired reaction temperature. The desired proportion of carbon monoxide was then added to the hydrogen stream, and one to two hours were allowed for the system to reach a steady state.

Gaseous products were analyzed periodically after the first hour. Liquid products were collected in the cold traps noted above. Thus, the turnover numbers for the gaseous products were averages of the samplings taken periodically after the first hour, while the turnover number for the liquid products were the average for the entire run.

Between each run, the carbon monoxide was shut off while the hydrogen continued to flow until the next reaction temperature was reached.

The reactor used at pressures above 800 psig was a bottom-agitated "Magnedrive" autoclave of the J. M. Berty design with a centrally positioned catalyst basket and a side product effluent line. It is of the type depicted in the paper by Berty, Hambrick, Malone and Ullock, entitled "Reactor for Vapor-Phase Catalytic Studies", presented as Preprint 42E at the Symposium on Advances in High-Pressure Technology-Part II, Sixty Fourth National Meeting of the American Institute of Chemical Engineers (AIChE), at New Orleans, La., on Mar. 16–20, 1969 and obtainable from AIChE at 345 East 47th, St. New York, N.Y. 10017. A variable speed, magnetically driven fan continuously recirculated the reaction mixture over the catalyst bed. The reactor was modified so that the effluent gas sample could be taken in a glass bulb right after the gas had been released to atmospheric pressure. Condensable liquid products were water cooled and removed from the exit stream in condenser at about 10° C. The non-condensable components of the exit stream were sampled periodically at the exit port and analyzed by gas chromatography. The flow of hydrogen and carbon monoxide was controlled and measured by separate flow meters.

About 3–4 grams of catalyst with about 6 cc. of volume, were placed in the catalyst basket. The remainder of the reactor space was filled with 3 mm. glass beads. The catalyst basket was charged to the reactor, and the reactor was sealed.

When the reactor was shown to be leak free, pure hydrogen was passed through the reactor, for 8 hours, at temperatures up to about 275° C. The desired proportion of carbon monoxide was then added to the reaction stream. A period of from 1–2 hours was allowed for the reactor to reach a steady state. The liquid product trap was then drained, a wet test meter reading was taken, and the time was noted at the beginning of a run. During the course of a run, one or more effluent gas samples are analyzed for hydrogen, carbon monoxide and volatile products. At the end of a run, the liquid product was collected, and the volume of effluent gas is noted. The liquid product was analyzed by gas chromatography.

Succeeding runs with the same catalyst may be made either at the same conditions or at new conditions of temperature or feed gas flow rates. If any of these conditions are changed, approximately 1–2 hr. is allowed for the reactor to come to a new steady-state before beginning a new run.

It is not necessary that the above procedures be followed exactly, as long as suitable reaction parameters are maintained.

The increased selectivity for oxygenated compounds of alkali-metal impregnated rhodium-tungsten catalysts over the same catalysts without alkali-metal impregnation is illustrated by Table 1 below. As shown, oxygenation activity is more than 17 times greater for the same catalyst under identical conditions, when 1 weight percent sodium is added. (Catalysts A and C). Methanation activity decreases to 1/7 of its former activity. Increasing the amount of sodium increases selectivity for oxygenates, although total CO-conversion is also decreased. (Catalysts C and D).

TABLE 1

Effect of Sodium in Supported Rhodium-Tungsten Catalysts on Activity and Selectivity for Synthesis Gas Reactions*

| Catalyst | +A | +B | +C | +D |
|---|---|---|---|---|
| Activity, μmole/g. min | | | | |
| Oxygenated Compounds | | | | |
| $CH_3OH$ | 0.73 | — | 3.11 | 1.79 |
| $C_2H_5OH$ | 0.17 | — | 4.02 | 1.57 |
| $n-C_3H_7OH$ | — | — | 0.29 | 0.15 |
| $CH_3COOCH_3$ | — | — | 0.99 | — |
| $CH_3COOC_2H_5$ | — | — | 0.78 | 0.50 |
| $CH_3COOH$ | — | — | 0.18 | 0.33 |
| Total (based on CO) | 1.07 | — | 18.47 | 8.04 |
| Hydrocarbons (based on CO) | | | | |
| $CH_4$ | 380.9 | 369.5 | 53.79 | 9.59 |
| $C_2-C_4$ | 18.99 | 11.79 | 9.85 | 1.54 |
| Total | 399.9 | 381.3 | 63.64 | 11.13 |
| Selectivity, C% | | | | |
| $C_2$ oxygenates | 0.06 | 0.0 | 13.3 | 22.2 |
| Total oxygenates | 0.16 | 0.0 | 17.0 | 30.7 |
| Hydrocarbons | 75.3 | 77.7 | 58.5 | 41.7 |

TABLE 1-continued

Effect of Sodium in Supported Rhodium-Tungsten Catalysts on Activity and Selectivity for Synthesis Gas Reactions*

| Catalyst | +A | +B | +C | +D |
|---|---|---|---|---|
| CO conversion % | 90.4 | 88.4 | 20.2 | 5.1 |

*Reaction conditions: T = 275° C., P = 230 psig, $H_2/CO$ = 2, GHSV = approximately 1,400.
+Catalyst Compositions:
A = Rhodium 3.05 wt. %; Tungsten 10.66 wt. 90.
B = Rhodium 2.94 wt. %; Tungsten 11.0 wt. %.
C = Rhodium 3.05 wt. %; Tungsten 10.66 wt. %; Sodium 1.0 wt. %.
D = Rhodium 3.20 wt. %; Tungsten 10.71 wt. %; Sodium 2.68 wt. %.

Table 2 below shows the effect of 1 weight percent sodium on oxygenation activity under optimal oxygenation conditions for rhodium-tungsten catalysts. Utilizing a hydrogen to carbon monoxide ratio of 0.5 produces measurable oxygenation activity for a rhodium-tungsten catalyst without alkali metal. However, addition of 1 weight percent sodium more than doubles oxygenation activity, with a five-fold increase in selectivity.

TABLE 2

Effect of Sodium in Supported Rhodium-Tungsten Catalysts on Activity and Selectivity for Synthesis Gas Reactions*

| Catalyst | +B | +C |
|---|---|---|
| Activity, μmole/g. min | | |
| Oxygenated compounds | | |
| $CH_3OH$ | 0.62 | 1.24 |
| $C_2H_5OH$ | 0.70 | 1.74 |
| $n\text{-}C_3H_7OH$ | 0.12 | 0.26 |
| $CH_3COOCH_3$ | 0.50 | 0.92 |
| $CH_3COOC_2H_5$ | 0.40 | 1.11 |
| $CH_3COOH$ | 0.69 | 0.78 |
| Total (based on CO) | 6.86 | 14.26 |
| Hydrocarbons (based on CO) | | |
| $CH_4$ | 42.76 | 14.37 |
| $C_2\text{-}C_4$ | 29.45 | 5.26 |
| $C_7\text{-}C_9$ | 1.34 | — |
| Total | 73.55 | 19.63 |
| Selectivity, C% | | |
| $C_2$ oxygenates | 4.2 | 23.5 |
| Total oygenates | 5.1 | 25.9 |
| Hydrocarbons | 54.5 | 37.7 |
| CO conversion, % | 10.3 | 4.2 |

*Reaction conditions: T = 275° C., P = 230 psig, $H_2/CO$ = 0.5, GHSV = 1,400.
+Catalyst compositions:
B = Rhodium 2.94 wt. %; Tungsten 11.0 wt. %.
C = Rhodium 3.05 wt. %; Tungsten 10.66 wt. %; Sodium 1.0 wt. %.

Tables 3 and 4 below illustrate the effect of supported rhodium-tungsten-sodium catalysts on the activity and selectivity for synthesis gas reactions carried out at high pressures in the Berty reactor. As shown, at higher pressure, methanol is the major product while the yields of methane and carbon dioxide are reduced.

TABLE 3

| Catalyst | +D |
|---|---|
| Activity, μmole/g. min. | |
| Oxygenated compounds | |
| $CH_3OH$ | 39.64 |
| $C_2H_5OH$ | 5.8 |
| $n\text{-}C_3H_7OH$ | 0.9 |
| $n\text{-}C_4H_9OH$ | 0.10 |
| $CH_3COOCH_3$ | 1.37 |
| $CH_3COOC_2H_5$ | 0.12 |
| Total (based on CO) | 58.93 |
| Hydrocarbons (based on CO) | |
| $CH_4$ | 26.37 |
| $C_2\text{-}C_4$ | 6.77 |
| Total | 33.14 |
| Selectivity, C% | |
| $C_2$ oxygenates | 11.4 |
| Total oxygenates | 41.9 |
| Hydrocarbons | 23.7 |
| CO conversion % | 24.7 |

*Reaction conditions: T = 255° C., P = 1575 psig, $H_2/CO$ = 2, GHSV = 1530
+Catalyst Composition Rhodium 3.20 wt. %; Tungsten 10.71 wt. %; sodium 2.68 wt. %.

TABLE 4

Effect of Sodium in Supported Rhodium-Tungsten Catalyst on Activity and Selectivity for Synthesis Gas Reactions at High Pressures

| Catalyst +C | Runs | | |
|---|---|---|---|
| | 1 | 2 | 3 |
| Temp. °C. | 240 | 242 | 242 |
| $H_2/CO$ | 0.5 | 0.5 | 2 |
| GHSV | 1,530 | 1,530 | 1,530 |
| psig | 3,470 | 3,475 | 3,475 |
| Activity, μmole/g. min | | | |
| Oxygenated Compounds | | | |
| $CH_3OH$ | 22.79 | 18.58 | 33.57 |
| $C_2H_5OH$ | 2.44 | 1.87 | 2.73 |
| $n\text{-}C_3H_7OH$ | 0.59 | 0.45 | 0.61 |
| $n\text{-}C_4H_9OH$ | 0.11 | 0.06 | 0.08 |
| $CH_3COOCH_3$ | — | — | — |
| $CH_3COOC_2H_5$ | 0.08 | 0.04 | — |
| $CH_3COOH$ | — | 0.08 | 0.09 |
| Total (based on CO) | 30.20 | 24.23 | 41.36 |
| Hydrocarbons (based on CO) | | | |
| $CH_4$ | 10.87 | 8.76 | 8.0 |
| $C_2\text{-}C_4$ | 1.27 | 0.70 | 0.80 |
| Total | 12.14 | 9.46 | 10.02 |
| Selectivity, C% | | | |
| $C_2$ oxygenates | 8.0 | 7.5 | 8.0 |
| Total oxygenates | 45.4 | 44.7 | 58.7 |
| Hydrocarbons | 18.5 | 17.5 | 14.2 |
| CO conversion % | 5.5 | 4.6 | 11.9 |

+Catalyst composition:
C = Rhodium 3.05 wt. %; Tungsten 10.66 wt. %, Sodium 1.0 wt. %.

The above results with sodium also suggest that other alkali metals, such as potassium, lithium, and cesium, may also be employed. Thus, similar results may be achieved using these other metals employing substantially the process disclosed herein, although some modifications may be necessary to achieve optimal results.

I claim:

1. A catalyst especially adapted for converting a gaseous mixture of carbon monoxide and hydrogen to oxygenated compounds consisting essentially of rhodium, tungsten and an alkali metal supported on alumina.

2. The catalyst of claim 1 containing from about 0.5 to 15.0 weight percent rhodium; 1.0 to 25.0 weight percent tungsten; and 0.5 to 10.0 weight percent of alkali metal.

3. The catalyst of claim 2 wherein said alkali metal is sodium.

4. The catalyst of claim 2 wherein said alumina is γ-alumina.

* * * * *